United States Patent [19]
Houlihan et al.

[11] 3,991,102
[45] Nov. 9, 1976

[54] 10-(2-SUBSTITUTED-AMINOETHYL)-10,11-DIHYDRO-5-METHYL-5H-DIBENZO[a,d]-CYCLOHEPTANES

[75] Inventors: William J. Houlihan, Mountain Lakes; Jeffrey Nadelson, Lake Parsippany, both of N.J.

[73] Assignee: Sandoz, Inc., E. Hanover, N.J.

[22] Filed: Apr. 22, 1974

[21] Appl. No.: 462,609

[52] U.S. Cl. .................... 260/501.1; 260/471 C; 260/501.21; 260/570.8; 424/316; 424/330
[51] Int. Cl.² ........................................ C07C 87/28
[58] Field of Search ............... 260/570.8 TC, 501.1, 260/501.21; 424/330

[56] References Cited
UNITED STATES PATENTS 3,649,692  3/1972  Humber .................. 260/570.8 X

OTHER PUBLICATIONS

Humber et al., "Journal of Medicinal Chemistry", vol. 14, No. 10, pp. 982–985, (1971).

Primary Examiner—Robert V. Hines
Attorney, Agent, or Firm—Gerald D. Sharkin; Robert S. Honor; Thomas O. McGovern

[57] ABSTRACT

10-(2-substituted-aminoethyl)-10,11-dihydro-5-methyl-2 or 3, 7 or 8-substituted or unsubstituted-5H-dibenzo[a,d]cycloheptenes, e.g., 10-(2-dimethylaminoethyl)-10,11-dihydro-5-methyl-5H-dibenzo[a,d]cycloheptene, are prepared by hydrogenating a corresponding 10-(2-dimethyl-aminoethyl)-10,11-dihydro-5-methylene-2 or 3, 7 or 8-substituted or unsubstituted-5H-dibenzo[a,d]cycloheptenes and are useful as anti-depressants.

9 Claims, No Drawings

10-(2-SUBSTITUTED-AMINOETHYL)-10,11-DIHYDRO-5-METHYL-5H-DIBENZO[a,d]CYCLOHEPTANES

This invention relates to 5-methyl-5H-dibenzo[a,d]cycloheptenes. More particularly, it relates to 10-(2-substituted aminoethyl)-10,11-dihydro-5-methyl-2' or 3, 7 or 8-substituted or unsubstituted-5H-dibenzo[a,d]cycloheptenes, acid addition salts thereof, and to processes for their preparation.

The compounds of this invention may be represented by the following structural formula:

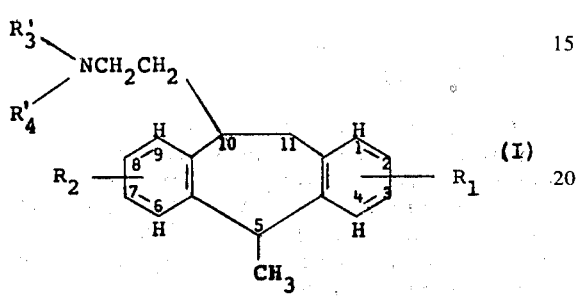

wherein
  $R_1$ and $R_2$ each independently represent hydrogen or fluoro, and
  $R_3'$ and $R_4'$ are each independently lower alkyl having 1 to 2 carbon atoms, i.e., methyl or ethyl, or one of $R_3'$ and $R_4'$ is hydrogen and the other is methyl.

The compounds of formula (I) are prepared according to the following reaction scheme:

where $R_1$, $R_2$, $R_3'$ and $R_4'$ are as defined above.

The compounds of formula (I) are prepared by hydrogenating a compound of the formula (II) in the presence of a noble metal catalyst such as palladium, platinum, rhodium and the like, optionally neat or on a support such as charcoal, at an atmosphere of from 35 to 100 psi, preferably 50 to 55 psi, in an inert organic solvent. Although the particular solvent used is not critical, the preferred solvents include the lower alkanols, e.g., methanol, ethanol and the like or acetic acid, preferably ethanol. The temperature of the reaction is not critical, but it is preferred that the reaction be carried out at a temperature between about 20° to 50° C., preferably room temperature. The reaction is run from about 5 to 24 hours, preferably from about 8 to 12 hours.

The compounds of formula (II) in which $R_3'$ and $R_4'$ are lower alkyl may be prepared by the following reaction scheme:

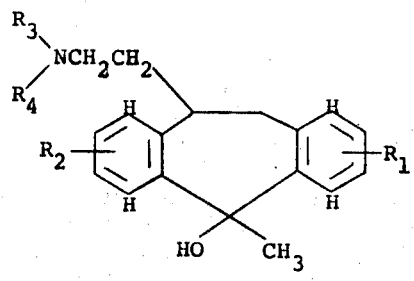

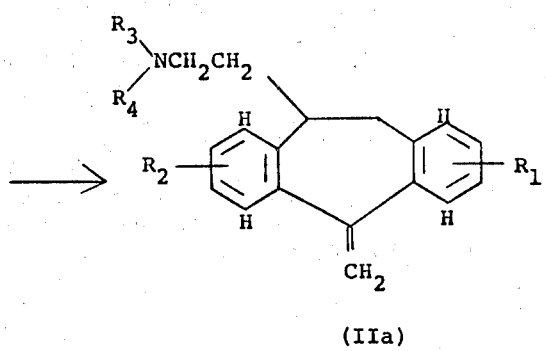

wherein
  $R_1$ and $R_2$ are as defined above; and
  $R_3$ and $R_4$ represent said lower alkyl.

The compounds of formula (IIa) may be prepared by treating a compound of formula (III) with a dehydrating agent such as dilute or concentrated mineral acids, e.g., sulfuric acid, hydrochloric acid and the like, iodine, phosphorus oxychloride, or thionyl chloride, an alkyl or arylsulfonyl chloride such as methanesulfonyl chloride or benzenesulfonyl chloride or an inorganic acid or Lewis acid used in the solid form. Examples of the last two acid types are potassium bisulphate, boric acid, aluminum oxide, and silicon dioxide. When phosphorus oxychloride or thionyl chloride or an alkyl or arylsulfonyl chloride is used as the dehydrating agent, it is preferred that an acid binding agent such as a lower alkyl tertiary amine wherein alkyl is defined as having 1 to 4 cabon atoms, e.g., triethylamine, be used. The reaction utilizing these dehydrating agents as well as that using the solid, inorganic acids and Lewis acids may be conveniently carried out in inert hydrocarbons such as benzene, toluene and the like, at a temperature from about 50° C. to the reflux temperature of the reaction medium, preferably the reflux temperature, for about 1 to 24 hours, preferably 1 to 4 hours. The preferred dehydration medium is 1M to 5M sulfuric acid. Neither the solvents nor the temperatures used are critical.

The compounds of formula (II) in which one of $R_3'$ and $R_4'$ is hydrogen and the other is methyl may be prepared according to the following reaction scheme:

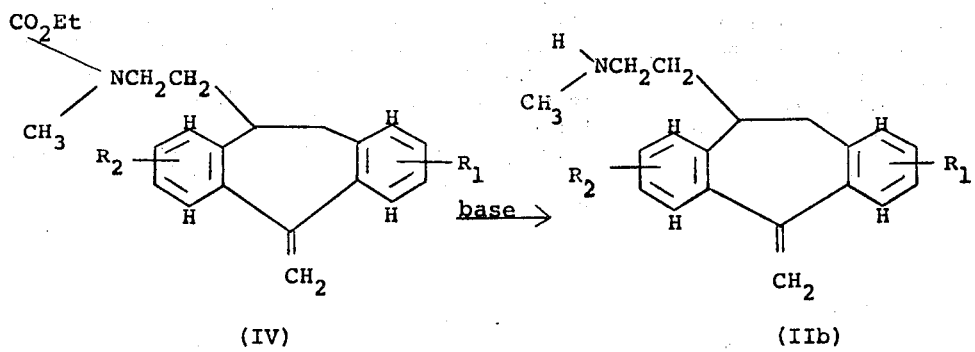

where $R_1$ and $R_2$ are as defined above and Et represents ethyl.

The compounds of formula (IIb) are prepared by treating a compound of the formula (IV) with an alkali metal hydroxide, such as potassium hydroxide, sodium hydroxide and lithium hydroxide, preferably potassium hydroxide in the presence of an inert organic solvent. Although the paticular solvent used is not critical, it is preferred that the reaction be carried out in the presence of dimethylacetamide, dimethylformamide or the lower alkanols, e.g., methanol, ethanol and the like, preferably ethanol. The temperature of the reacton is not critical, but it is preferred that the reaction be run from about 80° to 150° C., preferably the reflux temperature of the solvent. The reaction is run from about 5 to 24 hours, preferably from about 8 to 12 hours.

The compounds of formula (IV) may be prepared according to the following reaction scheme:

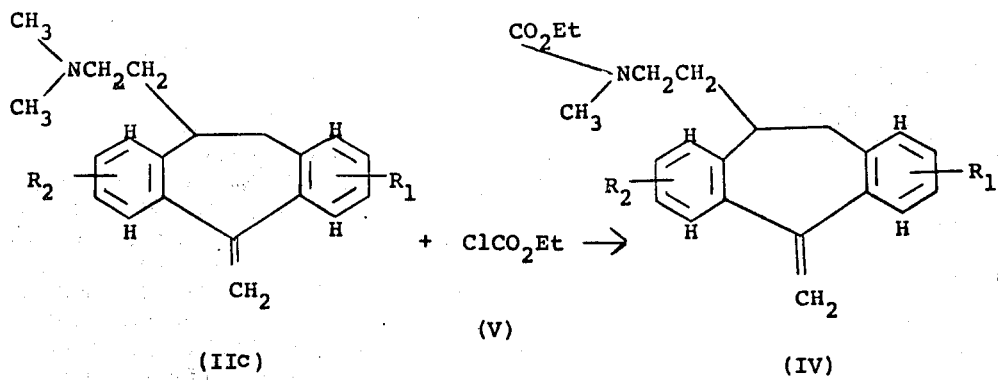

where Et represents ethyl, and
$R_1$ and $R_2$ are as defined above.

The compounds of formula (IV) are prepared by treating a compound of the formula (IIc) with a compound of the formula (V) in the presence of an inert organic solvent. Although the particular solvent employed is not critical, it is preferred that the reaction be carried out in the presence of the aromatic hydrocarbons such as benzene, toluene, xylene and the like, preferably toluene. The temperature of the reaction is not critical, but it is preferred that the reaction be run from about 80° to 180° C., preferably the reflux temperature of the solvent. The reaction is run from about 12 to 48 hours, preferably from about 16 to 20 hours.

The compounds of formulae (I) and (II) may be recovered using conventional techniques such as crystallization, evaporation, or filtration.

Certain of the compounds of formula (III) are known and may be prepared by methods disclosed in the literature. Those compounds of formula (III) not specifically disclosed may be prepared by analogous methods from known materials.

It will be understood that certain of the compounds of formulae (I) and (II) exist in form of racemic mixtures of optically active isomers or diastereoisomers. The separation and recovery of the respective isomers may be readily accomplished employing conventional techniques and such isomers are included within the scope of this invention.

The compounds of formula (I) are useful because they possess pharmacological activity in animals. More particularly, the compounds of formula (I) are useful as anti-depressant agents as indicated by their activity in male Wistar rats (weighing 180–200 grams) given intraperitoneally 25 mg/kg of the test compound. One hour later, 16.0 c/mM (New England Nuclear) in a volume of 30 μl of Merles solution of $3^H$-norepinephrine is administered according to the method of Noble et al, Life Sci., 6:281–291, 1967. The anti-depressant activity is measured according to the method of Neff and Costa, Life.Sci., 5:951–959, 1966, as modified by Snyder et al, J. Pharmacol. Exp. Therap., 164:90–102, 1968, as a reduction in the neuronal uptake of $3^H$-norepinephrine, as indicated by the ability of the test compound to reduce the total $3^H$-norepinephrine in the brain and a reduction in the $3^H$-norepinephrine specific activity.

When so utilized, the compounds may be combined with one or more pharmaceutically acceptable carrier or adjuvant. They may be administered orally or parenterally and, depending upon the compound employed and the mode of administration, the exact dosage utilized may vary.

Furthermore, the compounds (I) may be similarly administered in the form of their non-toxic pharmaceutically acceptable acid addition salts. Such salts possess the same order of activity as the free base, are readily prepared by reacting the base with an appropriate acid and, accordingly, are included within the scope of the invention. Representative of such salts are the mineral acid salts, such as the hydrochloride, hydrobromide, sulfate, phosphate and the like; and the organic acid salts, such as succinate, benzoate, acetate, p-toluenesulfonate, benzenesulfonate, maleate and the like.

As noted above, the compounds of formula (I) exist as optical isomers. In some cases, greater pharmacological activity or other beneficial attributes may be found for a particular isomer and, in such instances, administration of such isomers may be preferred.

In general, satisfactory results are obtained when the compounds are administered as anti-depressants at a daily dosage of from about 0.5 to 100 milligrams per kilogram of animal body weight. This daily dosage is preferably given in divided doses, e.g., 2 to 4 times a day, or in sustained release form. For most large animals, the total daily dosage is from about 30 to 750 milligrams and dosage forms suitable for internal administration comprise from about 7.5 to 375 milligrams of the compound in admixture with a solid or liquid pharmaceutical carrier or diluent.

A representative formulation suitable for oral administration 2 to 4 times a day in the treatment of depression is a capsule prepared by standard encapsulating techniques which contains the following:

| Ingredients | Weight (mg.) |
| --- | --- |
| 10-(2-dimethylaminoethyl)-10,11-dihydro-5-methyl-5H-dibenzo[a,d]-cycloheptene | 100 |
| Inert solid diluent (starch, lactose, kaolin) | 200 |

EXAMPLE 1

10-(2-dimethylaminoethyl)-10,11-dihydro-5-methylene-5H-dibenzo[a,d]cycloheptene.

A mixture of 8 g. (0.027 mole) of 10-(2-dimethylaminoethyl)-10,11-dihydro-5-methyl-5H-dibenzo[a,d]cyclohepten-5-ol and 250 ml. 2M-sulfuric acid is refluxed for 2 hours. The mixture is cooled in ice and made basic by the addition of solid potassium hydroxide. The mixture is extraced with methylene chloride. The methylene chloride is washed with water, dried over anhydrous magnesium sulfate and evapored in vacuo. The oily residue is distilled at 140° C/0.5 mm and the distillate is dissolved in ethanol. The resulting precipitate is filtered and recrystallized from diethylether-ethanol 1:1 to give the product 10-(2-dimethylaminoethyl)-10,11-dihydro-5-methylene-5H-dibenzo[a,d]cycloheptene, m.p. 171° to 172 C.

Following the above procedure and using an equivalent amount of ferric chloride in place of sulfuric acid, there is obtained the identical product.

Again, following the above procedure and using in place of 10-(2-dimethylaminoethyl)-10,11-dihydro-5-methyl-5H-dibenzo[a,d]cyclohepten-5-ol an equivalent amount of a. 10-(2-dimethylaminoethyl)-10,11-dihydro-2,7-difluoro-5-methyl-5H-dibenzo[a,d]cyclohepten-5-ol,
b. 10-(2-dimethylaminoethyl)-10,11-dihydro-7-fluoro-5-methyl-5H-dibenzo[a,d]cyclohepten-5-ol,
c. 10-(2-dimethylaminoethyl)-10,11-dihydro-8-fluoro-5-methyl-5H-dibenzo[a,d]cyclohepten-5-ol,
d. 10-(2-diethylaminoethyl)-10,11-dihydro-5-methyl-5H-dibenzo[a,d]cyclohepten-5-ol, or
e. 10-(2-dimethylaminoethyl)-10,11-dihydro-2-fluoro-5-methyl-5H-dibenzo[a,d]cyclohepten-5-ol, there is obtained a. 10-(2-dimethylaminoethyl)-10,11-dihyro-2,7-difluoro-5-methylene-5H-dibenzo[a,d]cycloheptene,
b. 10-(2-dimethylaminoethyl)-10,11-dihydro-7-fluoro-5-methylene-5H-dibenzo[a,d]cycloheptene,
c. 10-(2-dimethylaminoethyl)-10,11-dihydro-8-fluoro-5-methylene-5H-dibenzo[a,d]cycloheptene,
d. 10-(2-diethylaminoethyl)-10,11-dihydro-5-methylene-5H-dibenzo[a,d]cycloheptene, or
e. 10-(2-dimethylaminoethyl)-10,11-dihydro-2-fluoro-5-methylene-5H-dibenzo[a,d]cycloheptene, respectively.

EXAMPLE 2

10-(2-dimethylaminoethyl)-10,11-dihydro-5-methyl-5H-dibenzo[a,d]-cycloheptene.

A mixture of 5.54 g. (0.02 mole) 10-(2-dimethylaminoethyl)-10,11-dihydro-5-methylene-5H-dibenzo[a,d]cycloheptene and 0.6 g 5% palladium on carbon in 60 ml. ethanol is hydrogenated at atmospheric pressure and room temperature. The hydrogenation is stopped after 1 equivalent of hydrogen is absorbed, the catalyst is removed by filtration and the filtrate concentrated to a small volume in vacuo. The concentrated filtrate is treated with 2.32 g. (0.02 mole) maleic acid in ethanol and the resulting solid is filtered and washed with cold ethanol to give 10,11-dihydro-10-(2-dimethylaminoethyl)-5-methyl-5H-dibenzo[a,d]cycloheptene maleate, m.p. 120°–122° C.

Following the above procedure and using in place of 10-(2-dimethylaminoethyl)-10,11-dihydro-5-methylene-5H-dibenzo[a,d]cycloheptene an equivalent amount of:

a. 10-(2-dimethylaminoethyl)-10,11-dihydro-2,7-difluoro-5-methylene-5H-dibenzo[a,d]cycloheptene,
b. 10-(2-dimethylaminoethyl)-10,11-dihydro-7-fluoromethylene-5H-dibenzo[a,d]cycloheptene,
c. 10-(2-dimethylaminoethyl)-10,11-dihydro-8-fluoro-5-methylene-5H-dibenzo[a,d]cycloheptene,
d. 10-(2-diethylaminoethyl)-10,11-dihydro-5-methylene-5H-dibenzo[a,d]cycloheptene, or
e. 10-(2-dimethylaminoethyl)-10,11-dihydro-2-fluoro-5-methylene-5H-dibenzo[a,d]cycloheptene, there is obtained a. 10-(2-dimethylaminoethyl)-10,11-dihydro-2,7-difluoro-5-methyl-5H-dibenzo[a,d]cycloheptene maleate,
b. 10-(2-dimethylaminoethyl)-10,11-dihydro-7-fluoro-5-methyl-5H-dibenzo[a,d]cycloheptene maleate,
c. 10-(2-dimethylaminoethyl)-10,11-dihydro-8-fluoro-5-methyl-5H-dibenzo[a,d]cycloheptene maleate,
d. 10-(2-diethylaminoethyl)-10,11-dihydro-5-methyl-5H-dibenzo[a,d]cycloheptene maleate, or
e. 10-(2-dimethylaminoethyl)-10,11-dihydro-2-fluoro-5-methyl-5H-dibenzo[a,d]cycloheptene maleate, respectively.

The 10-(2-dimethylaminoethyl)-10,11-dihydro-5-methyl-5H-dibenzo[a,d]cycloheptene maleate is an effective anti-depressant agent when orally administered to an animal suffering from a depression at a dosage of 100 mg. four times per day.

EXAMPLE 3

10-(2-methylaminoethyl)-10,11-dihydro-5-methylene-5H-dibenzo[a,d]-cycloheptene.

A mixture of 15.2 g. (0.055 mole) of 10-(2-dimethylaminoethyl)-10,11-dihydro-5-methylene-5H-dibenzo[a,d]cycloheptene and 23.6 g. (0.218 mole) of ethylchloroformate in 125 ml. of toluene is refluxed under a nitrogen atmosphere for 18 hours. The excess solvent and reagent is removed by evaporation in vacuo. The resulting oil product is dissolved in a solution of 175 ml. of ethanol, 17 ml. of water and 35 g. (0.625 mole) of potassium hydroxide and refluxed for 10 hours. The solvents are removed in vacuo and the resulting layers are separated between ether and water. The ether is then extracted twice with 2N hydrochloric acid and the resulting aqueous acid is then made basic and extracted with ether. The excess solvent is then dried and evaporated and the resulting oil is dissolved in isopropyl alcohol and treated with hydrochloric gas. The residue is then filtered and recrystallized from isopropyl alcohol to give 10-(2-methylaminoethyl)-10,11-dihydro-5-methylene-5H-dibenzo[a,d]cycloheptene hydrochloride, m.p. 176°–177° C.

Following the above procedure and using in place of 10-(2-dimethylaminoethyl)-10,11-dihydro-5-methylene-5H-dibenzo[a,d]cycloheptene, an equivalent amount of a. 10-(2-dimethylaminoethyl)-10,11-dihydro-2,7-difluoro-5H-dibenzo[a,d]cycloheptene,
b. 10-(2-dimethylaminoethyl)-10,11-dihydro-7-fluoro-5H-dibenzo[a,d]cycloheptene,
c. 10-(2-dimethylaminoethyl)-10,11-dihydro-8-dihydro-8-fluoro-5H-dibenzo[a,d]cycloheptene, or
d. 10-(2-dimethylaminoethyl)-10,11-dihydro-2-fluoro-5H-dibenzo[a,d]cycloheptene, there is obtained the hydrochloride salt of a. 10-(2-methylaminoethyl)-10,11-dihydro-2,7-difluoro-5H-dibenzo[a,d]cycloheptene,
b. 10-(2-methylaminoethyl)-10,11-dihydro-7-fluoro-5H-dibenzo[a,d]cycloheptene,
c. 10-(2-methylaminoethyl)-10,11-dihydro-8-fluoro-5H-dibenzo[a,d]cycloheptene, or
d. 10-(2-methylaminoethyl)-10,11-dihydro-2-fluoro-5H-dibenzo[a,d]cycloheptene, respectively.

What is claimed is:
1. A compound of the formula

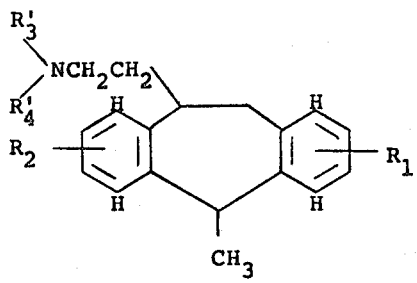

wherein
$R_1$ and $R_2$ each independently represent hydrogen or fluoro, and
$R_3'$ and $R_4'$ are independently lower alkyl having 1 to 2 carbon atoms, or one of $R_3'$ and $R_4'$ is hydrogen and the other is methyl.

2. A compound of the formula

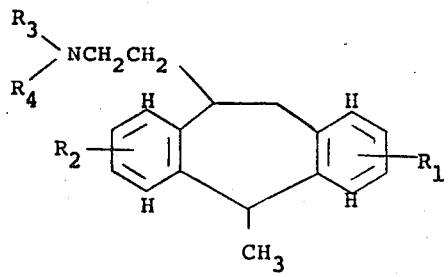

where
$R_3$ and $R_4$ are independently lower alkyl having 1 to 2 carbon atoms, and
$R_1$ and $R_2$ are as defined in claim 1, or a pharmaceutically acceptable acid addition salt thereof.

3. A compound of the formula

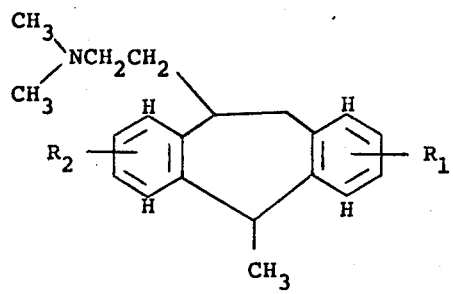

where $R_1$ and $R_2$ are as defined in claim 1, or a pharmaceutically acceptable acid addition salt thereof.

4. A compound of the formula

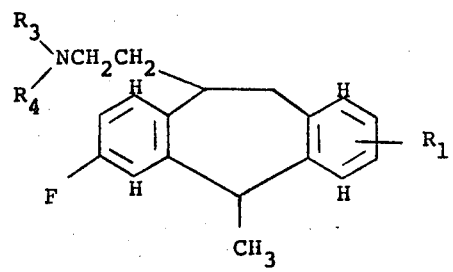

where $R_1$, $R_3$ and $R_4$ are as defined in claim 1, or a pharmaceutically acceptable acid addition salt thereof.

5. A compound of the formula

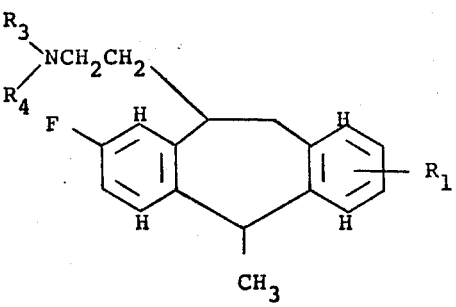

where $R_1$, $R_3$ and $R_4$ are as defined in claim 1, or a pharmaceutically acceptable acid addition salt thereof.

6. A compound of the formula

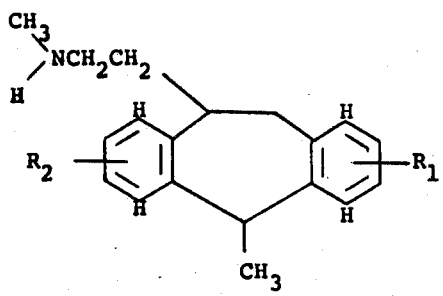

where $R_1$ and $R_2$ are as defined in claim 1, or a pharmaceutically acceptable acid addition salt thereof.

7. A pharmaceutically acceptable acid addition salt of a compound of claim 1.

8. The compound of claim 2 which is 10-(2-dimethylaminoethyl)-10,11-dihydro-5-methyl-5H-dibenzo[a,d]cycloheptene.

9. The compound of claim 2 which is 10-(2-dimethylaminoethyl)-10,11-dihydro-5-methyl-5H-dibenzo[a,d]cycloheptene maleate.

* * * * *